(12) United States Patent
Smith et al.

(10) Patent No.: US 8,685,112 B1
(45) Date of Patent: Apr. 1, 2014

(54) AMINE SALT ACTIVATION OF PEROXYCARBOXYLIC ACIDS

(71) Applicant: Ecolab USA Inc., St. Paul, MN (US)

(72) Inventors: Kim R. Smith, Woodbury, MN (US); Erik C. Olson, Savage, MN (US); Benjamin F. Reid, Medina, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

(21) Appl. No.: 13/661,352

(22) Filed: Oct. 26, 2012

(51) Int. Cl.
*C11D 3/395* (2006.01)

(52) U.S. Cl.
USPC .......................... 8/137; 8/101; 8/107; 8/111

(58) Field of Classification Search
USPC ...................... 8/101, 107, 111, 137
See application file for complete search history.

(56) References Cited

U.S. PATENT DOCUMENTS

2004/0147423 A1* 7/2004 Scialla et al. ............. 510/372

* cited by examiner

*Primary Examiner* — Eisa Elhilo
(74) *Attorney, Agent, or Firm* — McKee, Voorhees & Sease, P.L.C.

(57) ABSTRACT

Treated peroxycarboxylic acid bleaching compositions and methods of using the same are provided to enhancing bleaching performance of various peroxycarboxylic acids. Peroxycarboxylic acid peroxycarboxylic acid compositions are combined with non-metal bleach activators, preferably polyethyleneimines. The invention further relates to methods employing the enhanced bleaching compositions.

20 Claims, 3 Drawing Sheets

AMINE SALT ACTIVATION OF PEROXYCARBOXYLIC ACIDS

FIELD OF THE INVENTION

The invention relates to the field of peroxycarboxylic acid bleaching compositions and methods of using the same. In particular, the invention relates to peroxycarboxylic acid bleaching compositions having improved antimicrobial and/or bleaching capability due to the addition of a polyethyleneimine bleach activator.

BACKGROUND OF THE INVENTION

Peracid compositions, namely peroxycarboxylic acid compositions, exhibit useful antimicrobial and bleaching activity. Conventional peroxycarboxylic acid compositions typically include short chain peroxycarboxylic acids or mixtures of short chain peroxycarboxylic acids and medium chain peroxycarboxylic acids, such as those disclosed in U.S. Pat. Nos. 5,200,189, 5,314,687, 5,409,713, 5,437,868, 5,489,434, 6,674,538, 6,010,729, 6,111,963, and 6,514,556, each of which is incorporated by reference in its entirety. Such peroxycarboxylic acids have low molecular weights, including for example peracetic acid.

There are limitations associated with peracid compositions, including peroxycarboxylic acids, such as the malodors associated with short chain peracids and the decomposition of peracid compositions over time. As a result, peracid compositions may exhibit a strong, sharp, irritating, or otherwise unacceptable odor. Another example of a limitation of use of malodorous peracids includes the use of hot water, such as in industrial laundry applications, as this increases volatility of the acids and further intensifies the malodor. However, despite the limitations of peroxycarboxylic acid compositions, they remain effective antimicrobial and bleaching agents. In addition, in various cleaning and bleaching applications there remains a need for more effective antimicrobial and/or bleaching agents, including the peroxycarboxylic acid compositions.

Accordingly, it is an objective of the claimed invention to develop peroxycarboxylic acid bleaching compositions having improved antimicrobial and bleaching profiles.

According to the invention, it is a particular object to develop peroxycarboxylic acid bleaching compositions having improved bleaching capability over peracetic acid.

A further object of the invention is to develop polyethyleneimine bleaching activators for various peroxycarboxylic acids, including peracetic acid.

BRIEF SUMMARY OF THE INVENTION

An advantage of the invention is the improvement in antimicrobial and/bleaching performance of various peroxycarboxylic acids, including peracetic acid. In particular, the bleaching performance of peroxycarboxylic acid (also referred to herein as a "peracid") bleaching compositions is significantly improved over peracetic acid. The present invention relates to peracid compositions including a bleach activator, preferably a metal-free polyethyleneimine bleach activator, and methods for generating and employing the enhanced bleaching peroxycarboxylic acid compositions. Typically, the compositions and methods according to the present invention incorporate one or more suitable polyethyleneimine agents.

In an embodiment, the present invention relates to an enhanced bleaching peroxycarboxylic acid composition comprising: at least one peroxycarboxylic acid; and a non-metal bleach activator, wherein the bleach activator is a polymeric nitrogen-containing compound that is effective for enhanced bleaching in comparison to the peroxycarboxylic acid alone and is present in a use solution in amounts from about 1 ppm to about 5000 ppm, and wherein the composition has a pH less than about 9.

In a further embodiment, the present invention relates to an enhanced bleaching peroxycarboxylic acid composition comprising: about 0.01 wt-% to 50 wt-% of at least one peroxycarboxylic acid; and about 0.0001 wt-% to 20 wt-% of a non-metal, polyethyleneimine bleach activator, wherein the bleach activator is effective for providing enhanced bleaching in comparison to the peroxycarboxylic acid alone and is present in a use solution in amounts from about 1 ppm to about 5000 ppm, and wherein the composition has a pH less than about 9.

In certain embodiments of the invention, the non-metal bleach activator is a polymeric nitrogen-containing compound, including for example polyethyleneimines. In further aspects, the polyethyleneimines may be substituted or non-substituted.

In further embodiments, the present invention relates methods of enhancing bleaching performance of peracid composition, comprising: providing a bleach activator to a peroxycarboxylic acid composition to form a peroxycarboxylic acid bleaching composition comprising: about 0.01 wt-% to 50 wt-% of at least one peroxycarboxylic acid; and about 0.0001 wt-% to 20 wt-% of a non-metal, polyethyleneimine bleach activator, wherein the bleach activator is effective for providing enhanced bleaching in comparison to the peroxycarboxylic acid alone and is present in a use solution in amounts from about 1 ppm to about 5000 ppm, and wherein the composition has a pH less than about 9; and contacting an object with peroxycarboxylic acid bleaching composition. The methods may also include a step of generating a cationic polymer from the bleach activator in the presence of a neutralizing acid, wherein the neutralizing acid includes the peroxycarboxylic acid, and wherein the cationic polymer is the acid salt of the bleach activator. The bleach activator may be provided to the peroxycarboxylic acid composition in a variety of ways, including for example, through a co-fed stream to form a use solution or it may be preformulated into a concentrate or ready-to-use composition according to embodiments of the invention.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENT

The present invention relates to improved bleaching compositions including a bleaching activator, such as a polyethyleneimine to stabilize and/or activate the peroxycarboxylic acid. The compositions of the invention have improved bleaching performance in comparison to non-activated peracid compositions. The compositions can be used on a variety of hard surfaces and methods of employing the same are provided within the scope of the invention.

The embodiments of this invention are not limited to particular peroxycarboxylic acid bleaching compositions and methods of generating and employing the same, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form. Numeric ranges recited within the specification are inclusive of the numbers defining the range and include each integer within the defined range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

As used herein, "agricultural" or "veterinary" objects or surfaces include animal feeds, animal watering stations and enclosures, animal quarters, animal veterinarian clinics (e.g. surgical or treatment areas), animal surgical areas, and the like.

The term "alkyl" or "alkyl groups," as used herein, refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups). Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage.

The first is a lethal, irreversible action resulting in complete microbial cell destruction or incapacitation. The second type of cell damage is reversible, such that if the organism is rendered free of the agent, it can again multiply. The former is termed bacteriocidal and the later, bacteriostatic. A sanitizer and a disinfectant are, by definition, agents which provide antibacterial or bacteriocidal activity. In contrast, a preservative is generally described as an inhibitor or bacteriostatic composition.

The phrase "health care surface," as used herein, refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.), or woven and non-woven surfaces (such as surgical garments, draperies, bed linens, bandages, etc.), or patient-care equipment (such as respirators, diagnostic equipment, shunts, body scopes, wheel chairs, beds, etc.), or surgical and diagnostic equipment. Health care surfaces include articles and surfaces employed in animal health care.

The term "heterocyclic group," as used herein (e.g. referring to substituted alkyls including a heterocyclic group), includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

The term "microorganisms," as used herein, refers to any noncellular or unicellular (including colonial) organism. Microorganisms include all prokaryotes. Microorganisms include bacteria (including cyanobacteria), lichens, microfungi, protozoa, virinos, viroids, viruses, and some algae. As used herein, the term "microbe" is synonymous with microorganism.

The term "object", as used herein, refers to a something material that can be perceived by the senses, directly and/or indirectly. Objects include a surface, including a hard surface (such as glass, ceramics, metal, natural and synthetic rock, wood, and polymeric), an elastomer or plastic, woven and non-woven substrates, a food processing surface, a health care surface, and the like. Objects also include a food product (and its surfaces); a body or stream of water or a gas (e.g., an air stream); and surfaces and articles employed in hospitality and industrial sectors.

The phrase "short chain carboxylic acid," as used herein, refers to a carboxylic acid that has characteristic bad, pungent, or acrid odor. Examples of short chain carboxylic acids include formic acid, acetic acid, propionic acid, and butyric acid.

The term "ware," as used herein, refers to items such as eating and cooking utensils, dishes, and other hard surfaces such as showers, sinks, toilets, bathtubs, countertops, windows, mirrors, transportation vehicles, and floors. As used herein, the term "warewashing" refers to washing, cleaning, or rinsing ware. Ware also refers to items made of plastic. Types of plastics that can be cleaned with the compositions according to the invention include but are not limited to, those that include polycarbonate polymers (PC), acrilonitrile-butadiene-styrene polymers (ABS), and polysulfone polymers (PS). Another exemplary plastic that can be cleaned using the compounds and compositions of the invention include polyethylene terephthalate (PET).

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and compositions of the present invention may comprise, consist essentially of, or consist of the components and ingredients of the present invention as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

Compositions

Peroxycarboxylic acid bleaching compositions having improved bleaching performance are provided according to the present invention. Beneficially, the peracids to be treated according to the invention may include both concentrated and ready-to-use peracid compositions, as well as include the combination of peracid compositions with the bleaching activators at a point of use. In an aspect, the peroxycarboxylic acid bleaching compositions may comprise, consist of or consist essentially of a peracid and a bleach activator. The peroxycarboxylic acid bleaching compositions may further include a surfactant. The peroxycarboxylic acid bleaching compositions may further include an additional oxidizing agent. In an additional aspect, the peroxycarboxylic acid bleaching compositions may include additional functional ingredients.

While an understanding of the mechanism is not necessary to practice the present invention, in some embodiments the peroxycarboxylic acid compositions incorporating a bleach activator provide improved bleaching activity in comparison to peracetic acid without the bleach activator. While the present invention is not limited to any particular mechanism of action, it is contemplated that in the presence of a peracid, a non-metal bleach activator, such as polyethyleneimine, becomes a cationic polymer that is the acid salt of the starting material (e.g. bleach activator such as polyethyleneimine) and provides enhanced attraction to negatively charged substrates such as many soils, stains, and hard surfaces. The combination of the particular polyethyleneimines with a peracid as at least a part of the neutralizing acid, results in at least a portion of the resulting cationic polymer becoming a further source of peracid oxygen bleach.

Peracids

A variety of peroxycarboxylic acids may be employed in the bleaching compositions according to the invention. In some embodiments of the invention at least one peroxycarboxylic acid is employed. According to an embodiment of the invention suitable peroxycarboxylic acids include ester peroxycarboxylic acids, alkyl ester peroxycarboxylic acids, sulfoperoxycarboxylic acids, and combinations of several different peroxycarboxylic acids, as described herein. Further description of suitable alkyl ester peroxycarboxylic acids and ester peroxycarboxylic acids according to the invention is included in U.S. Pat. Nos. 7,816,555 and 7,622,606, both entitled "Peroxycarboxylic Acid Compositions with Reduced Odor," hereby expressly incorporated herein in its entirety by reference, including without limitation all drawings and chemical structures contained therein.

The terms "peracid," "peroxyacid," "percarboxylic acid" and "peroxycarboxylic acid" as used herein, refer synonymously to acids having the general formula $R(CO_3H)_n$. The R group can be saturated or unsaturated as well as substituted or unsubstituted. As described herein, R is an alkyl, arylalkyl, cycloalkyl, aromatic, heterocyclic, or ester group, such as an alkyl ester group. N is one, two, or three, and named by prefixing the parent acid with peroxy. Ester groups are defined as R groups including organic moieties (such as those listed above for R) and ester moieties. Exemplary ester groups include aliphatic ester groups, such as $R_1OC(O)R_2$, where each of $R_1$ and $R_2$ can be aliphatic, preferably alkyl, groups described above for R. Preferably $R_1$ and $R_2$ are each independently small alkyl groups, such as alkyl groups with 1 to 5 carbon atoms. As one skilled in the art shall appreciate, peroxycarboxylic acids are not as stable as carboxylic acids, their stability generally increases with increasing molecular weight. Thermal decomposition of these acids can generally proceed by free radical and nonradical paths, by photodecomposition or radical-induced decomposition, or by the action of metal ions or complexes. Percarboxylic acids can be made by the direct, acid catalyzed equilibrium action of hydrogen peroxide with the carboxylic acid, by autoxidation of aldehydes, or from acid chlorides, and hydrides, or carboxylic anhydrides with hydrogen or sodium peroxide.

Exemplary peroxycarboxylic acids useful in the compositions of the present invention include peroxyformic, peroxyacetic, peroxypropionic, peroxybutanoic, peroxypentanoic, peroxyhexanoic, peroxyheptanoic, peroxyoctanoic, peroxynonanoic, peroxydecanoic, peroxyundecanoic, peroxydodecanoic, peroxylactic, peroxycitric, peroxymaleic, peroxyascorbic, peroxyhydroxyacetic (peroxyglycolic), peroxyoxalic, peroxymalonic, peroxysuccinic, peroxyglutaric, peroxyadipic, peroxypimelic, peroxysuberic, and peroxysebacic acid, and mixtures thereof. Useful peroxycarboxylic acids also include the ester peroxycarboxylic acids described herein and compositions of the present invention including those ester peroxycarboxylic acids. Peroxy forms of carboxylic acids with more than one carboxylate moiety can have one or more of the carboxyl moieties present as peroxycarboxyl moieties. These peroxycarboxylic acids have been found to provide good antimicrobial action with good stability in aqueous mixtures. In a preferred embodiment, the composition of the invention utilizes a combination of several different peroxycarboxylic acids.

In an embodiment, the bleaching composition of the invention utilizes a combination of several different peroxycarboxylic acids, including mixed peracid compositions. The terms "mixed" or "mixture" when used relating to "peracid composition," "peroxycarboxylic acid composition," "peracids" or "peroxycarboxylic acids" refer to a composition or mixture including more than one peracid, such as a peroxycarboxylic acid, such as a composition or mixture including peroxyacetic acid and peroxyoctanoic acid.

According to one embodiment, the composition includes one or more small $C_2$-$C_4$ peroxycarboxylic acids, one or more large $C_8$-$C_{12}$ peroxycarboxylic acids, one or more ester peroxycarboxylic acids, one or more alkyl ester peroxycarboxylic acids, and/or one or more mono- or di-peroxycarboxylic acid having up to 12 carbon atoms. According to a further embodiment, the peroxycarboxylic acid has from 2 to 12 carbon atoms. According to an embodiment, the peroxycarboxylic acids include peroxyacetic acid (POAA) (or peracetic acid having the formula $CH_3COOOH$) and/or peroxyoctanoic acid (POOA) (or peroctanoic acid having the formula, for example, of n-peroxyoctanoic acid: $CH_3$ $(CH_2)_6$ COOOH).

According to an additional embodiment of the invention one or more sulfoperoxycarboxylic acid may also be used in the compositions disclosed herein. As used herein, the term "sulfoperoxycarboxylic acid," "sulfonated peracid," or "sulfonated peroxycarboxylic acid" refers to the peroxycarboxylic acid form of a sulfonated carboxylic acid. In some embodiments, the sulfonated peracids of the present invention are mid-chain sulfonated peracids. As used herein, the term "mid-chain sulfonated peracid" refers to a peracid compound that includes a sulfonate group attached to a carbon that is at least one carbon (e.g., the three position or further) from the carbon of the percarboxylic acid group in the carbon backbone of the percarboxylic acid chain, wherein the at least one carbon is not in the terminal position. As used herein, the term "terminal position," refers to the carbon on the carbon backbone chain of a percarboxylic acid that is furthest from the percarboxyl group.

According to an embodiment of the invention, sulfoperoxycarboxylic acids have the following general formula:

wherein $R_1$ is hydrogen, or a substituted or unsubstituted alkyl group; $R_2$ is a substituted or unsubstituted alkyl group; X is hydrogen, a cationic group, or an ester forming moiety; or salts or esters thereof.

In some embodiments, $R_1$ is a substituted or unsubstituted $C_m$ alkyl group; X is hydrogen a cationic group, or an ester forming moiety; $R_2$ is a substituted or unsubstituted $C_n$ alkyl group; m=1 to 10; n=1 to 10; and m+n is less than 18, or salts, esters or mixtures thereof. In some embodiments, $R_1$ is hydrogen. In other embodiments, $R_1$ is a substituted or unsubstituted alkyl group. In some embodiments, $R_1$ is a substituted or unsubstituted alkyl group that does not include a cyclic alkyl group. In some embodiments, $R_1$ is a substituted alkyl group. In some embodiments, $R_1$ is an unsubstituted $C_1$-$C_9$ alkyl group. In some embodiments, $R_1$ is an unsubstituted $C_7$ or $C_8$ alkyl. In other embodiments, $R_1$ is a substituted $C_8$-$C_{10}$ alkyl group. In some embodiments, $R_1$ is a substituted $C_8$-$C_{10}$ alkyl group is substituted with at least 1, or at least 2 hydroxyl groups. In still yet other embodiments, $R_1$ is a substituted $C_1$-$C_9$ alkyl group. In some embodiments, $R_1$ is a substituted $C_1$-$C_9$ substituted alkyl group is substituted with at least 1 $SO_3H$ group. In other embodiments, $R_1$ is a $C_9$-$C_{10}$ substituted alkyl group. In some embodiments, $R_1$ is a substituted $C_9$-$C_{10}$ alkyl group wherein at least two of the carbons on the carbon backbone form a heterocyclic group. In some embodiments, the heterocyclic group is an epoxide group.

In further embodiments, $R_2$ is a substituted $C_1$-$C_{10}$ alkyl group. In some embodiments, $R_2$ is a substituted $C_8$-$C_{10}$ alkyl. In some embodiments, $R_2$ is an unsubstituted $C_6$-$C_9$ alkyl. In other embodiments, $R_2$ is a $C_8$-$C_{10}$ alkyl group substituted with at least one hydroxyl group. In some embodiments, $R_2$ is a $C_{10}$ alkyl group substituted with at least two hydroxyl groups. In other embodiments, $R_2$ is a Cg alkyl group substituted with at least one $SO_3H$ group. In some embodiments, $R_2$ is a substituted $C_9$ group, wherein at least two of the carbons on the carbon backbone form a heterocyclic group. In some embodiments, the heterocyclic group is an epoxide group. In some embodiments, $R_1$ is a $C_8$-$C_9$ substituted or unsubstituted alkyl, and $R_2$ is a $C_7$-$C_8$ substituted or unsubstituted alkyl.

Further description of suitable sulfoperoxycarboxylic acids, and methods of making the same, according to the invention are included in U.S. patent application Ser. Nos. 12/568,493 and 12/413,189, entitled "Sulfoperoxycarboxylic Acids, Their Preparation and Methods of Use as Bleaching and Antimicrobial Agents," hereby expressly incorporated herein in its entirety by reference, including without limitation all drawings and chemical structures contained therein.

According to an additional embodiment of the invention one or more carboxylic acids may also be used in the compositions disclosed herein. Generally, carboxylic acids have the formula R—COOH wherein the R can represent any number of different groups including aliphatic groups, alicyclic groups, aromatic groups, heterocyclic groups, and ester groups, such as alkyl ester groups, all of which can be saturated or unsaturated and/or substituted or unsubstituted. Carboxylic acids can have one, two, three, or more carboxyl groups. Preferred ester groups include aliphatic ester groups, such as $R_1OC(O)R_2$—where each of $R_1$ and $R_2$ can be aliphatic, preferably alkyl, groups described above for R. Preferably $R_1$ and $R_2$ are each independently small alkyl groups, such as alkyl groups with 1 to 4 carbon atoms.

The composition of the invention can employ carboxylic acids containing as many as 22 carbon atoms. Examples of suitable carboxylic acids include formic, acetic, propionic, butanoic, pentanoic, hexanoic, heptanoic, octanoic, nonanoic, decanoic, undecanoic, dodecanoic, lactic, maleic, ascorbic, citric, hydroxyacetic (glycolic), neopentanoic, neoheptanoic, neodecanoic, oxalic, malonic, succinic, glutaric, adipic, pimelic suberic, and sebacic acid. Examples of suitable alkyl ester carboxylic acids include monomethyl oxalic acid, monomethyl malonic acid, monomethyl succinic acid, monomethyl glutaric acid, monomethyl adipic acid, monomethyl pimelic acid, monomethyl suberic acid, and monomethyl sebacic acid; monoethyl oxalic acid, monoethyl malonic acid, monoethyl succinic acid, monoethyl glutaric acid, monoethyl adipic acid, monoethyl pimelic acid, monoethyl suberic acid, and monoethyl sebacic acid; monopropyl oxalic acid, monopropyl malonic acid, monopropyl succinic acid, monopropyl glutaric acid, monopropyl adipic acid, monopropyl pimelic acid, monopropyl suberic acid, and monopropyl sebacic acid, in which propyl can be n- or isopropyl; and monobutyl oxalic acid, monobutyl malonic acid, monobutyl succinic acid, monobutyl glutaric acid, monobutyl adipic acid, monobutyl pimelic acid, monobutyl suberic acid, and monobutyl sebacic acid, in which butyl can be n-, iso-, or t-butyl.

In some embodiments, the carboxylic acid for use with the compositions of the present invention is a $C_2$ to $C_{12}$ carboxylic acid. In some embodiments, the carboxylic acid for use with the compositions of the present invention is a $C_5$ to $C_{11}$ carboxylic acid. In some embodiments, the carboxylic acid for use with the compositions of the present invention is a $C_1$ to $C_4$ carboxylic acid. Examples of suitable carboxylic acids include, but are not limited to, formic, acetic, propionic, butanoic, pentanoic, hexanoic, heptanoic, octanoic, nonanoic, decanoic, undecanoic, dodecanoic, as well as their branched isomers, lactic, maleic, ascorbic, citric, hydroxyacetic, neopentanoic, neoheptanoic, neodecanoic, oxalic, malonic, succinic, glutaric, adipic, pimelic subric acid, and mixtures thereof. Carboxylic acids that are generally useful include ester carboxylic acids, such as alkyl ester carboxylic acids.

In some embodiments, the compositions of the present invention include a combination of peroxycarboxylic acids and optionally carboxylic acids. According to an embodiment, the compositions of the present invention include at least one sulfoperoxycarboxylic acid and at least one carboxylic and/or percarboxylic acid. In some embodiments, the compositions of the present invention include at least two, at least three, or at least four or more carboxylic and/or peroxycarboxylic acids.

The chemical structures herein, including the peroxycarboxylic acids, are drawn according to the conventional standards known in the art. Thus, where an atom, such as a carbon atom, as drawn appears to have an unsatisfied valency, then that valency is assumed to be satisfied by a hydrogen atom, even though that hydrogen atom is not necessarily explicitly drawn. The structures of some of the compounds of this invention include stereogenic carbon atoms. It is to be understood that isomers arising from such asymmetry (e.g., all enantiomers and diastereomers) are included within the scope of this invention unless indicated otherwise. That is, unless otherwise stipulated, any chiral carbon center may be of either (R)— or (S)-stereochemistry. Such isomers can be obtained in substantially pure form by classical separation techniques and by stereochemically-controlled synthesis. Furthermore, alkenes can include either the E- or Z-geometry, where appropriate. In addition, the compounds of the present invention may exist in unsolvated as well as solvated forms with acceptable solvents such as water, THF, ethanol, and the like. In general, the solvated forms are considered equivalent to the unsolvated forms for the purposes of the present invention.

In a preferred embodiment, the peroxycarboxylic acids, carboxylic acids and/or sulfoperoxycarboxylic acid are provided in an aqueous solution.

Exemplary methods and apparatus for making peroxycarboxylic acids are disclosed for example in U.S. Pat. Nos. 7,547,421 and 8,017,082, both entitled "Apparatus and Method for Making a Peroxycarboxylic Acid," hereby expressly incorporated herein in its entirety by reference. Additional methods and apparatus may be employed and are not intended to limit the scope of the present invention.

Bleach Activator

The compositions of the invention include a bleach activator to enhance the bleaching performance of peracid compositions. Notably, as referred to herein, the bleach activator is not a compound that reacts with a hydrogen peroxide (or other oxidizing agent) to form a peracid (or the activated peroxygen bleaching compound). Instead, the bleach activator according to the invention enhances bleaching performance of the peracid composition itself. In an aspect, a non-metal bleaching activator is combined with a peracid or peracid composition to enhance bleaching performance. In an aspect of the invention the bleach activator improves bleaching performance of the peracid in comparison to peracetic acid alone.

In an aspect, the bleach activator is a nitrogen-containing compound, preferably a polymeric amine. In a further aspect, the bleach activator is a polymeric amine or a polyamine. Preferred polymeric amines include, for example, polyethyleneimine compounds (PEI) and/or its derivatives. Polyethyleneimines may include primary, secondary or tertiary amine compounds. The polyethyleneimine compounds and/or its derivatives may include linear and/or branched polyethyleneimines. Still further, polyethyleneimines and/or its derivatives can vary significantly in molecular weight, topology and shape, including for example linear, branched or comb-like structures as a result of ring-opening polymerization of the ethylenimine. See Angelescu et al., Langmuir, 27, 9961-9971 (2011), which is incorporated herein by reference in its entirety. According to an aspect of the invention, the bleach activator may be a linear and/or branched polyethyleneimine.

Linear polyethyleneimines are made by the cationic polymerization of oxazoline and oxazine derivatives. Methods for preparing linear PEIs are more fully described in Advances in Polymer Science, Vol. 102, pgs. 171-188, 1992 (references 6-31) which is incorporated in its entirety herein by reference. Polyethyleneimines can also be made by the polymerization of aziridine to afford a polymeric amine often containing primary, secondary, and tertiary amine functionality. Commercial preparation of PEIs is generally acid-catalyzed reactions to open the ring of ethyleneimine, also known as aziridine as shown below.

-continued

Often the commercial production of ethyleneimine, which is subsequently catalyzed to open to form PEIs, is prepared through sulfuric acid esterification of ethanolamine, such as shown below:

Suitable polyethyleneimine compounds useful in the present invention may contain a mixture of primary, secondary, and tertiary amine substituents. The mixture of primary, secondary, and tertiary amine substituents may be in any ratio, including for example in the ratio of about 1:1:1 to about 1:2:1 with branching every 3 to 3.5 nitrogen atoms along a chain segment. Alternatively, suitable polyethyleneimine compounds may be primarily one of primary, secondary or tertiary amine substituents.

Exemplary PEI products include multifunctional cationic polyethyleneimines with branched polymer structures according to the following formulas (—(CH$_2$—CH$_2$—NH)$_n$—), with a molecular mass of 43.07 (as repeating units). In certain aspects the formula (—(CH$_2$—CH$_2$—NH)$_n$—) has a value of n that is at least 10 to $10^5$, and wherein the nitrogen to carbon ratio is 1:2. PEI polymers have the general following polymer structure:

PEI products can also be represented by the following general formula, which may vary according to substitutions, size, molecular weight, branching, and the like:

wherein x is an integer that is 1 or greater and y is an integer that is 1 or greater than 1. Preferably, wherein x is an integer from about 1 to about 120,000, preferably from about 2 to about 60,000, more preferably from about 3 to about 24,000 and y is an integer from about 1 to about 60,000, preferably from about 2 to about 30,000, more preferably from about 3 to about 12,000.

Various commercial polyethyleneimines are available, including for example those sold under the tradename Lupasol® (BASF), including for example Lupasol® FG, Lupasol® G, Lupasol® PR 8515, Lupasol® WF, Lupasol® G 20/35/100, Lupasol® HF, Lupasol® P, Lupasol® PS, Lupasol® PO 100, Lupasol® PN 50/60, and Lupasol® SK. Such exemplary polyethyleneimines are available as anhydrous polyethyleneimines and/or modified polyethyleneimines provided in aqueous solutions or methoyxypropanol (Lupasol® PO 100). The molar mass of the polyethyleneimines, including modified polyethyleneimines can vary from about 800 g/mol to at least 2,000,000 g/mol.

In certain aspects the polymeric amine bleach activators, and preferably the PEI bleach activators, may be a branched, spherical polymeric amine. In further aspects, the molecular weight of the polymeric amine bleach activators or PEI bleach activators is from about 100 Daltons to about 2 million Daltons (PEI-2,000,000), more preferably from about 100 Daltons to about 1 million Daltons (PEI-1,000,000), more preferably from about 500 Daltons to about 500 kDa (PEI-500,000), more preferably from about 500 Daltons to about 50 kDa (PEI-50,000), more preferably from about 800 Daltons to about 50 kDa (PEI-50,000), more preferably from about 800 Daltons to about 10 kDa (PEI-10,000).

In further aspects, the charge density of the PEI or PEI salt is from about 15 mEq/g to about 25 mEq/g, more preferably from about 16 mEq/g to about 20 mEq/g. Commercially-available examples of such preferred PEIs include the BASF products LUPASOL® WF (25 kDa; 16-20 mEq/g) and Lupasol® FG (800 Daltons; 16-20 mEq/g), and the BASF products in the SOKALAN® family of polymers, e.g., SOKALAN® HP20, SOKALAN® HP22 G, and the like.

In an aspect, a polymeric amine may contain other substituents and/or and copolymers. For example, a polymeric amine may also include substituents, including for example ethoxylates and propoxylates. In an aspect of the invention, the polymeric amine, such as a polyethyleneimines, are derivatized with ethylene oxide (EO) and/or propylene oxide (PO) side chains. In an exemplary aspect of the invention ethoxylated PEIs may be heavily branched, wherein the substitutable hydrogens on the primary and secondary nitrogens are replaced with ethoxylated chains containing varying degrees of repeating units, such as the following polymer structure (generic for PEI$_{20}$EO):

In an aspect, the bleach activator is a polyethyleneimine polymer with ethyleneoxide chains. Ethoxylation of PEIs increases the solubility of the bleach activator according to the invention.

A polymeric amine may also include endcap substituents, including for example ethylenediamine. A variety of substituents and/or copolymers may be included in order to modify the solubility or any other physical characteristics of a particular polymeric amine employed as a bleach activator according to the invention.

Because of the presence of amine groups, PEI can be protonated with acids to form a PEI salt from the surrounding medium resulting in a product that is partially or fully ionized depending on pH. For example, about 73% of PEI is protonated at pH 2, about 50% of PEI is protonated at pH 4, about 33% of PEI is protonated at pH 5, about 25% of PEI is protonated at pH 8 and about 4% of PEI is protonated at pH 10. In general, PEIs can be purchased as their protonated or unprotonated form with and without water. An example of a segment of a branched protonated polyethyleneimine (PEI salt) is shown below:

The counter ion of each protonated nitrogen center is balanced with an anion of an acid obtained during neutralization. Examples of protonated PEI salts include, but are not limited to, PEI-hydrochloride salt, PEI-sulfuric acid salt, PEI-nitric acid salt, PEI-acetic acid salt PEI fatty acid salt and the like. In fact, any acid can be used to protonate PEIs resulting in the formation of the corresponding PEI salt compound.

In an aspect of the invention, the bleach activators are preferably polymeric amines. In an alternative aspect, the bleaching activators are non-substituted polymeric amines.

In an aspect, the bleach activator may be provided in any form, including a liquid or a solid. In embodiments employing a solid bleach activator, the solid is diluted for liquid use, which may vary depending upon the preferred methods of use according to the invention disclosed herein.

In an aspect, the use levels of the bleach activator in use solution are sufficient to improve the bleaching performance of a peracid or peracid composition. In an aspect, the use levels of the bleach activator in use solution are sufficient to provide superior bleaching performance in comparison to a peracetic acid composition without the bleach activator. In some embodiments, a use solution of a peroxycarboxylic acid bleaching composition according to the invention includes from about 1 ppm to about 5000 ppm bleach activator. In a preferred embodiment, a use solution of a peroxycarboxylic acid bleaching composition includes from about 5 ppm to about 1000 ppm bleach activator, more preferably from about 10 ppm to about 500 ppm bleach activator. One skilled in the art would be able to calculate ratios of bleach activator to peracid, preferably polyethyleneimine to peracid, in a concentrated peracid product that would afford these levels.

In an aspect, the peroxycarboxylic acid bleaching compositions in a use solution have a pH that at least partially neutralizes the bleach activator, such as a polyethyleneimine bleach activator by the peracid. Typically, a polyethyleneimine bleach activator will be at least partially neutralized by a peracid at a pH of about less than about 9, less than about 8, and less than about 7. Preferably the pH of a use solution is from about 1 to about 9, preferably from about 1 to about 8, and more preferably from about 1 to about 7. It is to be understood that all ranges and values between these ranges and values are encompassed by the present invention.

Oxidizing Agents

In some aspects of the invention, the peroxycarboxylic acid bleaching compositions include at least one oxidizing agent. When present in the peroxycarboxylic acid compositions, any of a variety of oxidizing agents may be employed, for example, hydrogen peroxide. The oxidizing agent can be present at an amount effective to convert a fatty acid, such as a carboxylic acid or a sulfonated carboxylic acid to a peroxycarboxylic acid or a sulfonated peroxycarboxylic acid. In some embodiments, the oxidizing agent can also have antimicrobial activity. In other embodiments, the oxidizing agent is present in an amount insufficient to exhibit antimicrobial activity and/or further improvement in bleaching activity.

Examples of inorganic oxidizing agents include the following types of compounds or sources of these compounds, or alkali metal salts including these types of compounds, or forming an adduct therewith: hydrogen peroxide, urea-hydrogen peroxide complexes or hydrogen peroxide donors of: group 1 (IA) oxidizing agents, for example lithium peroxide; sodium peroxide; group 2 (IIA) oxidizing agents, for example magnesium peroxide, calcium peroxide, strontium peroxide, barium peroxide; group 12 (IIB) oxidizing agents, for example zinc peroxide; group 13 (IIIA) oxidizing agents, for example boron compounds, such as perborates, for example sodium perborate hexahydrate of the formula $Na_2[B_2(O_2)_2(OH)_4]6H_2O$ (also called sodium perborate tetrahydrate); sodium peroxyborate tetrahydrate of the formula $Na_2B_2(O_2)_2[(OH)_4]4H_2O$ (also called sodium perborate trihydrate); sodium peroxyborate of the formula $Na_2[B_2(O_2)_2(OH)_4]$ (also called sodium perborate monohydrate); group 14 (IVA) oxidizing agents, for example persilicates and peroxycarbonates, which are also called percarbonates, such as persilicates or peroxycarbonates of alkali metals; group 15 (VA) oxidizing agents, for example peroxynitrous acid and its salts; peroxyphosphoric acids and their salts, for example, perphosphates; group 16 (VIA) oxidizing agents, for example peroxysulfuric acids and their salts, such as peroxymonosulfuric and peroxydisulfuric acids, and their salts, such as persulfates, for example, sodium persulfate; and group VIIa oxidizing agents such as sodium periodate, potassium perchlorate. Other active inorganic oxygen compounds can include transition metal peroxides; and other such peroxygen compounds, and mixtures thereof.

In some embodiments, the compositions of the present invention employ one or more of the inorganic oxidizing agents listed above. Suitable inorganic oxidizing agents include ozone, hydrogen peroxide, hydrogen peroxide adduct, group IIIA oxidizing agent, or hydrogen peroxide donors of group VIA oxidizing agent, group VA oxidizing agent, group VIIA oxidizing agent, or mixtures thereof. Suitable examples of such inorganic oxidizing agents include percarbonate, perborate, persulfate, perphosphate, persilicate, or mixtures thereof.

The peroxycarboxylic acid compositions preferably include a hydrogen peroxide constituent. Beneficially, hydrogen peroxide in combination with the peroxycarboxylic acids provides certain antimicrobial actions against microorganisms. Additionally, hydrogen peroxide can provide an effervescent action which can irrigate any surface to which it is applied. Hydrogen peroxide works with a mechanical flushing action once applied which further cleans the surface. An additional advantage of hydrogen peroxide is the food compatibility of this composition upon use and decomposition. For example, combinations of peroxyacetic acid, peroxyoctanoic acid, and hydrogen peroxide result in acetic acid, octanoic acid, water, and oxygen upon decomposition, all of which are food product compatible and do not adversely affect an apparatus, handling or processing, or other surfaces to which the peroxycarboxylic acid composition is applied.

Surfactants

In some aspects of the invention, the peroxycarboxylic acid bleaching compositions also include at least one surfactant. Surfactants may be included in the bleaching compositions to enhance microbial efficacy, increase solubility of the peroxycarboxylic acid and/or to maintain the pH of the composition. According to an embodiment of the invention, a surfactant may include a hydrotrope coupler or solubilizer, which can be used to ensure that the composition remains phase stable.

Surfactants suitable for use with the bleaching compositions of the present invention are disclosed for example in Kirk-Othmer, Encyclopedia of Chemical Technology, Third Edition, volume 8, pages 900-912, which is herein incorporated by reference in its entirety. Particularly suitable surfactants for use according to embodiments of the invention include, nonionic surfactants, anionic surfactants, amphoteric surfactants, and cationic surfactants.

In additional aspects of the invention, the peroxycarboxylic acid compositions do not employ any surfactants. In additional aspects of the invention, the peroxycarboxylic acid compositions do not employ amine oxide surfactants.

Nonionic Surfactants

Suitable nonionic surfactants suitable for use with the compositions of the present invention include alkoxylated surfactants. Suitable alkoxylated surfactants include EO/PO copolymers, capped EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates, such as Dehypon LS-54 (R-$(EO)_5(PO)_4$) and Dehypon LS-36 (R-$(EO)_3(PO)_6$); and capped alcohol alkoxylates, such as Plurafac LF221 and Tegoten EC11; mixtures thereof, or the like.

The semi-polar type of nonionic surface active agents is another class of nonionic surfactant useful in compositions of the present invention. Semi-polar nonionic surfactants include the amine oxides, phosphine oxides, sulfoxides and their alkoxylated derivatives.

Amine oxides are tertiary amine oxides corresponding to the general formula:

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkylene or a hydroxyalkylene group containing 2 to 3 carbon atoms; and n ranges from 0 to about 20. An amine oxide can be generated from the corresponding amine and an oxidizing agent, such as hydrogen peroxide.

Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

Anionic Surfactants

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl) glucamine sulfates, and sulfates of alkylpolysaccharides such as the sulfates of alkylpolyglucoside, and the like. Also included are the alkyl sulfates, alkyl poly(ethyleneoxy)ether sulfates and aromatic poly(ethyleneoxy) sulfates such as the sulfates or condensation products of ethylene oxide and nonyl phenol (usually having 1 to 6 oxyethylene groups per molecule).

Anionic sulfonate surfactants suitable for use in the present compositions also include alkyl sulfonates, the linear and branched primary and secondary alkyl sulfonates, and the aromatic sulfonates with or without substituents.

Anionic carboxylate surfactants suitable for use in the present compositions include carboxylic acids (and salts), such as alkanoic acids (and alkanoates), ester carboxylic acids (e.g. alkyl succinates), ether carboxylic acids, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionic surfactants include alkyl or alkylaryl ethoxy carboxylates of the following formula:

$$R—O—(CH_2CH_2O)_n(CH_2)_m—CO_2X \qquad (3)$$

in which R is a $C_8$ to $C_{22}$ alkyl group or in which $R^1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In some embodiments, n is an integer of 4 to 10 and m is 1. In some embodiments, R is a $C_8$-$C_{16}$ alkyl group. In some embodiments, R is a $C_{12}$-$C_{14}$ alkyl group, n is 4, and m is 1.

In other embodiments, R is and $R^1$ is a $C_6$-$C_{12}$ alkyl group. In still yet other embodiments, $R^1$ is a $C_9$ alkyl group, n is 10 and m is 1.

Such alkyl and alkylaryl ethoxy carboxylates are commercially available. These ethoxy carboxylates are typically available as the acid forms, which can be readily converted to the anionic or salt form. Commercially available carboxylates include, Neodox 23-4, a $C_{12-13}$ alkyl polyethoxy (4) carboxylic acid (Shell Chemical), and Emcol CNP-110, a $C_9$ alkylaryl polyethoxy (10) carboxylic acid (Witco Chemical). Carboxylates are also available from Clariant, e.g. the product Sandopan® DTC, a $C_{13}$ alkyl polyethoxy (7) carboxylic acid.

Amphoteric Surfactants

Amphoteric, or ampholytic, surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. Amphoteric surfactants are subdivided into two major classes known to those of skill in the art and described in "Surfactant Encyclopedia" Cosmetics & Toiletries, Vol. 104 (2) 69-71 (1989), which is herein incorporated by reference in its entirety. The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Amphoteric surfactants can be synthesized by methods known to those of skill in the art. For example, 2-alkyl hydroxyethyl imidazoline is synthesized by condensation and ring closure of a long chain carboxylic acid (or a derivative) with dialkyl ethylenediamine.

Commercial amphoteric surfactants are derivatized by subsequent hydrolysis and ring-opening of the imidazoline ring by alkylation—for example with chloroacetic acid or ethyl acetate. During alkylation, one or two carboxy-alkyl groups react to form a tertiary amine and an ether linkage with differing alkylating agents yielding different tertiary amines.

Long chain imidazole derivatives having application in the present invention generally have the general formula:

wherein R is an acyclic hydrophobic group containing from about 8 to 18 carbon atoms and M is a cation to neutralize the charge of the anion, generally sodium. Commercially prominent imidazoline-derived amphoterics that can be employed in the present compositions include for example: Cocoamphopropionate, Cocoamphocarboxy-propionate, Cocoamphoglycinate, Cocoamphocarboxy-glycinate, Cocoamphopropyl-sulfonate, and Cocoamphocarboxy-propionic acid. Amphocarboxylic acids can be produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled, Zwitterion Surfactants.

Long chain N-alkylamino acids are readily prepared by reaction $RNH_2$, in which R=$C_8$-$C_{1-18}$ straight or branched chain alkyl, fatty amines with halogenated carboxylic acids. Alkylation of the primary amino groups of an amino acid leads to secondary and tertiary amines. Alkyl substituents may have additional amino groups that provide more than one reactive nitrogen center. Most commercial N-alkylamine acids are alkyl derivatives of beta-alanine or beta-N(2-carboxyethyl) alanine Examples of commercial N-alkylamino acid ampholytes having application in this invention include alkyl beta-amino dipropionates, $RN(C_2H_4COOM)_2$ and $RNHC_2H_4COOM$. In an embodiment, R can be an acyclic hydrophobic group containing from about 8 to about 18 carbon atoms, and M is a cation to neutralize the charge of the anion.

Suitable amphoteric surfactants include those derived from coconut products such as coconut oil or coconut fatty acid. Additional suitable coconut derived surfactants include as part of their structure an ethylenediamine moiety, an alkanolamide moiety, an amino acid moiety, e.g., glycine, or a combination thereof; and an aliphatic substituent of from about 8 to 18 (e.g., 12) carbon atoms. Such a surfactant can also be considered an alkyl amphodicarboxylic acid. These amphoteric surfactants can include chemical structures represented as: $C_{12}$-alkyl-C(O)—NH—$CH_2$—$CH_2$—$N^+(CH_2$—$CH_2$—$CO_2NO_2$—$CH_2$—$CH_2$—OH or $C_{1-2}$-alkyl-C(O)—N(H)—$CH_2$—$CH_2$—$N^+(CH_2$—$CO_2Na)_2$—$CH_2$—$CH_2$—OH.

Disodium cocoampho dipropionate is one suitable amphoteric surfactant and is commercially available under the tradename Miranol™ FBS from Rhodia Inc., Cranbury, N.J. Another suitable coconut derived amphoteric surfactant with the chemical name disodium cocoampho diacetate is sold under the tradename Mirataine™ JCHA, also from Rhodia Inc., Cranbury, N.J.

A typical listing of amphoteric classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Zwitterionic Surfactants

Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate.

Betaine and sultaine surfactants are exemplary zwitterionic surfactants for use herein. A general formula for these compounds is:

wherein $R^1$ contains an alkyl, alkenyl, or hydroxyalkyl radical of from 8 to 18 carbon atoms having from 0 to 10 ethylene oxide moieties and from 0 to 1 glyceryl moiety; Y is selected from the group consisting of nitrogen, phosphorus, and sulfur atoms; $R^2$ is an alkyl or monohydroxy alkyl group containing 1 to 3 carbon atoms; x is 1 when Y is a sulfur atom and 2 when Y is a nitrogen or phosphorus atom, $R^3$ is an alkylene or hydroxy alkylene or hydroxy alkylene of from 1 to 4 carbon atoms and Z is a radical selected from the group consisting of carboxylate, sulfonate, sulfate, phosphonate, and phosphate groups.

Examples of zwitterionic surfactants having the structures listed above include: 4-[N,N-di(2-hydroxyethyl)-N-octadecylammonio]-butane-1-carboxylate; 5-[S-3-hydroxypropyl-S-hexadecylsulfonio]-3-hydroxyp entane-1-sulfate; 3-[P,P-diethyl-P-3,6,9-trioxatetracosanephosphonio]-2-hydroxypropane-1-phosphate; 3-[N,N-dipropyl-N-3-dodecoxy-2-hydroxypropyl-ammonio]-propane-1-phosphonate; 3-(N,N-dimethyl-N-hexadecylammonio)-propane-1-sulfonate; 3-(N,N-dimethyl-N-hexadecylammonio)-2-hydroxy-propane-1-sulfonate; 4-[N,N-di(2(2-hydroxyethyl)-N(2-hydroxydodecyl)ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and S[N,N-di(3-hydroxypropyl)-N-hexadecylammonio]-2-hydroxy-pentane-1-sulfate. The alkyl groups contained in said detergent surfactants can be straight or branched and saturated or unsaturated.

The zwitterionic surfactant suitable for use in the present compositions includes a betaine of the general structure:

These surfactant betaines typically do not exhibit strong cationic or anionic characters at pH extremes nor do they show reduced water solubility in their isoelectric range. Unlike "external" quaternary ammonium salts, betaines are compatible with anionics. Examples of suitable betaines include coconut acylamidopropyldimethyl betaine; hexadecyl dimethyl betaine; $C_{12-14}$ acylamidopropylbetaine; $C_{8-14}$ acylamidohexyldiethyl betaine; 4-$C_{14-16}$ acylmethylamidodiethylammonio-1-carboxybutane; $C_{16-18}$ acylamidodimethylbetaine; $C_{12-16}$ acylamidopentanediethylbetaine; and $C_{12-16}$ acylmethylamidodimethylbetaine.

Sultaines useful in the present invention include those compounds having the formula $(R(R^1)_2N^+R^2SO^{3-}$, in which R is a $C_6$-$C_{18}$ hydrocarbyl group, each $R^1$ is typically independently $C_1$-$C_3$ alkyl, e.g. methyl, and $R^2$ is a $C_1$-$C_6$ hydrocarbyl group, e.g. a $C_1$-$C_3$ alkylene or hydroxyalkylene group.

A typical listing of zwitterionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch). Each of these references is herein incorporated in their entirety.

In an embodiment, the compositions of the present invention include a betaine. For example, the compositions can include cocoamido propyl betaine.

Cationic Surfactants

Cationic surfactants preferably include, more preferably refer to, compounds containing at least one long carbon chain hydrophobic group and at least one positively charged nitrogen. The long carbon chain group may be attached directly to the nitrogen atom by simple substitution; or more preferably indirectly by a bridging functional group or groups in so-called interrupted alkylamines and amido amines. Such functional groups can make the molecule more hydrophilic and/or more water dispersible, more easily water solubilized by co-surfactant mixtures, and/or water soluble. For increased water solubility, additional primary, secondary or tertiary amino groups can be introduced or the amino nitrogen can be quaternized with low molecular weight alkyl groups. Further, the nitrogen can be a part of branched or straight chain moiety of varying degrees of unsaturation or of a saturated or unsaturated heterocyclic ring. In addition, cationic surfactants may contain complex linkages having more than one cationic nitrogen atom.

The surfactant compounds classified as amine oxides, amphoterics and zwitterions are themselves typically cationic in near neutral to acidic pH solutions and can overlap surfactant classifications. Polyoxyethylated cationic surfactants generally behave like nonionic surfactants in alkaline solution and like cationic surfactants in acidic solution.

The simplest cationic amines, amine salts and quaternary ammonium compounds can be schematically drawn thus:

in which, R represents a long alkyl chain, R', R", and R'" may be either long alkyl chains or smaller alkyl or aryl groups or hydrogen and X represents an anion. The amine salts and quaternary ammonium compounds are preferred for practical use in this invention due to their high degree of water solubility.

The majority of large volume commercial cationic surfactants can be subdivided into four major classes and additional sub-groups known to those or skill in the art and described in "Surfactant Encyclopedia", Cosmetics & Toiletries, Vol. 104 (2) 86-96 (1989). The first class includes alkylamines and their salts. The second class includes alkyl imidazolines. The third class includes ethoxylated amines. The fourth class includes quaternaries, such as alkylbenzyldimethylammonium salts, alkyl benzene salts, heterocyclic ammonium salts, tetra alkylammonium salts, and the like. Cationic surfactants are known to have a variety of properties that can be beneficial in the present compositions. These desirable properties can include detergency in compositions of or below neutral pH, antimicrobial efficacy, thickening or gelling in cooperation with other agents, and the like.

Cationic surfactants useful in the compositions of the present invention include those having the formula $R^1_mR^2_xY_LZ$ wherein each $R^1$ is an organic group containing a straight or branched alkyl or alkenyl group optionally substituted with up to three phenyl or hydroxy groups and optionally interrupted by up to four of the following structures:

or an isomer or mixture of these structures, and which contains from about 8 to 22 carbon atoms. The $R^1$ groups can additionally contain up to 12 ethoxy groups. m is a number from 1 to 3. Preferably, no more than one $R^1$ group in a molecule has 16 or more carbon atoms when m is 2 or more than 12 carbon atoms when m is 3. Each $R^2$ is an alkyl or hydroxyalkyl group containing from 1 to 4 carbon atoms or a benzyl group with no more than one $R^2$ in a molecule being benzyl, and x is a number from 0 to 11, preferably from 0 to 6. The remainder of any carbon atom positions on the Y group are filled by hydrogens. Y is can be a group including, but not limited to:

p = about 1 to 12 or a mixture thereof. Preferably, L is 1 or 2, with the Y groups being separated by a moiety selected from $R^1$ and $R^2$ analogs (preferably alkylene or alkenylene) having from 1 to about 22 carbon atoms and two free carbon single bonds when L is 2. Z is a water soluble anion, such as a halide, sulfate, methylsulfate, hydroxide, or nitrate anion, particularly preferred being chloride, bromide, iodide, sulfate or methyl sulfate anions, in a number to give electrical neutrality of the cationic component.

Additional Functional Ingredients

In some embodiments, the compositions of the present invention can include other additional functional ingredients. Additional functional ingredients suitable for use with the bleaching compositions of the present invention include, but are not limited to, acidulants, stabilizing agents, e.g., chelating agents, sequestrants and/or crystallization inhibitors, threshold agents, buffers, detergents, wetting agents, defoaming agents, thickeners, foaming agents, hydrogen peroxide reducing agents (e.g. catalase enzymes), solidification agents, aesthetic enhancing agents (i.e., colorants, odorants, or perfumes) and other cleaning agents. In some aspects, the compositions do not include the use of any phosphonate chelant due to the use of a PEI bleach activator.

These additional ingredients can be preformulated with the compositions of the invention or added to the system before, after, or substantially simultaneously with the addition of the compositions of the present invention.

In an aspect of the invention, the peroxycarboxylic acid compositions do not employ enzymes. In still further aspects of the invention, the peroxycarboxylic acid compositions do not employ enzymes and/or surfactants.

Exemplary Compositions

Various embodiments of the invention are shown in Tables 1 and 2 depicting suitable concentrate and ready-to-use, respectively, peroxycarboxylic acid bleaching compositions according to the invention.

TABLE 1

(concentrate)

| | Wt-% | Wt-% | Wt-% |
|---|---|---|---|
| Peracid | 0.1-80 | 1-50 | 5-30 |
| Carboxylic Acid | 0.1-80 | 1-50 | 5-30 |
| Bleach Activator | 0.01-80 | 0.1-50 | 1-30 (1-50,000 ppm) |
| Oxidizing Agent | 0.1-80 | 1-50 | 5-30 |
| Surfactant | 0-50 | 0-30 | 0-20 |
| Additional Functional Ingredients | 0-50 | 0-20 | 0-10 |
| Water | 0-50 | 0-30 | 0-20 |

TABLE 2

(ready-to-use)

| | Wt-% or ppm ranges | Wt-% or ppm ranges | Wt-% or ppm ranges |
|---|---|---|---|
| Peracid | 0.01-50 | 0.1-40 | 1-20 |
| Carboxylic Acid | 0.01-50 | 0.1-40 | 1-20 |
| Bleach | 0.0001-50 | 0.0001-20 | 0.0001-10 |
| Activator | (1-5000 ppm) | (5-1000 ppm) | (10-500 ppm) |
| Oxidizing Agent | 0.01-50 | 0.1-40 | 1-20 |
| Surfactant | 0-50 | 0.1-20 | 1-20 |
| Additional Functional Ingredients | 0-50 | 0.1-20 | 1-10 |
| Water | 0-80 | 0-50 | 0-30 |

According to the invention, the amount of peroxycarboxylic acid in use and concentrate compositions can range up to the limits at which the peroxycarboxylic acid can be dissolved or suspended in the composition.

The peroxycarboxylic acid bleaching compositions include both concentrate compositions and use compositions. For example, a concentrate composition can be diluted, for example with water, to form a use composition. In an embodiment, a concentrate composition can be diluted to a use solution before to application to an object. Primarily for reasons of economics, the concentrate can be marketed and an end user can dilute the concentrate with water or an aqueous diluent to a use solution.

The level of active components (and percent actives) in the concentrate composition is dependent on the intended dilution factor and the desired activity of the peracid compound. Generally, a dilution of about 1 fluid ounce to about 10 gallons of water to about 10 fluid ounces to about 1 gallon of water is used for aqueous compositions of the present invention. In some embodiments, higher use dilutions can be employed if elevated use temperature or extended exposure time (greater than 30 seconds) can be employed. In the typical use locus, the concentrate is diluted with a major proportion of water using commonly available tap or service water mixing the materials at a dilution ratio of about 3 to about 40 ounces of concentrate per 100 gallons of water.

In some embodiments, such as use in laundry applications, the concentrated compositions can be diluted at a dilution ratio of about 0.1 g/L to about 100 g/L concentrate to diluent, about 0.5 g/L to about 10.0 g/L concentrate to diluent, about 1.0 g/L to about 4.0 g/L concentrate to diluent, or about 1.0 g/L to about 2.0 g/L concentrate to diluent. In other embodiments, a use composition can include about 0.01 to about 10 wt-% of a concentrate composition and about 90 to about 99.99 wt-% diluent; or about 0.1 to about 1 wt-% of a concentrate composition and about 99 to about 99.9 wt-% diluent. Amounts of an ingredient in a use composition can be calculated from the amounts listed above for concentrate compositions and these dilution factors.

As one skilled in the art shall appreciate based on the disclosure of the present invention, the enhanced bleaching compositions of the invention can be formulated as a liquid concentrate composition and/or use compositions. The peracid compositions of the present invention can also be formulated as a gel, an aerosol, a gas, a wax, a solid, or a powder, or as a solution or suspension containing such a composition.

Each of the compositions can be formulated by combining the various ingredients. The peroxycarboxylic acid compositions are formulated to provide an equilibrium composition, wherein the peracid exists in equilibrium with its corresponding carboxylic acid and hydrogen peroxide (or other oxidizing agent).

In an aspect of the invention, the peroxycarboxylic acid bleaching compositions have at least the same or substantially similar stability as conventional, commercially-available peroxycarboxylic acid compositions. In some embodiments, the compositions of the present invention are stable for at least about 2 years at room temperature. In further embodiments, the compositions of the present invention are stable for at least about 1 year at room temperature.

Methods of Enhancing Bleaching of Peracid Composition

Peroxycarboxylic acid bleaching compositions are generated according to the methods of the invention to provide superior bleaching efficacy in comparison to peracid compositions, namely peracetic acid. The methods of enhancing bleaching performance of a peroxycarboxylic acid compositions may comprise, consist of and/or consist essentially of providing a peracid to be treated and contacting the peracid with a bleach activator. The methods may further comprise, consist of and/or consist essentially of generating a cationic polymer from the bleach activator in the presence of a neutralizing acid, wherein the neutralizing acid includes the peracid to be treated. In an aspect, the cationic polymer is the acid salt of the bleach activator (e.g. polyethyleneimine) and results in enhanced bleaching of the peracid composition due to the enhanced attraction to negatively charged substrates (e.g. soils, stains, and hard surfaces). The methods may further comprise, consist of and/or consist essentially of contacting an object with the peracid and bleach activator (i.e. peroxycarboxylic acid bleaching composition).

In a preferred aspect, a peracid is contacted with at least one bleach activator. Preferably the bleach activator is a polymeric amine, preferably a polyethyleneimine.

The contacting of the peracid with the bleach activator may occur through the formulation of a peroxycarboxylic acid bleaching composition according to the invention, such as adding a bleach activator to a concentrate and/or use solution of a peracid. In a further aspect, the contact of the peracid with the bleach activator may occur through the direct application of the bleach activator to a peracid composition, including for example, dissolving the bleach activator into the peracid or providing in a co-fed stream to form a use solution. In a further alternative aspect, the contacting of the peracid with the bleach activator may occur at a point of use by mixing or co-dispensing the peracid and the bleach activator.

The step of contacting the peracid with the bleach activator may occur for a period of time ranging from a few seconds to a few minutes. The step of contacting the peracid with the bleach activator may occur for a period of time ranging from a few minutes to a few hours. Without being limited to a particular theory of the invention, there is no increased benefit to contacting the peracid and bleach activator for more than a few hours. However, the use of longer contact periods, such as for example, storing a treated peroxycarboxylic acid bleaching composition is within the scope of the invention.

The methods of the invention are suitable for use according to a broad temperature range. Beneficially, the step of contacting the peracid with the bleach activator may occur at a temperature range from about 10 to 70° C., preferably about 20 to 60° C. to increase efficacy.

Methods of Using the Bleaching Compositions

According to one embodiment of the invention, the peroxycarboxylic acid bleaching compositions are employed for antimicrobial or bleaching activity of the peracid of the compositions. The compositions of the present invention can be used as antimicrobial or bleaching compositions for a variety of substrates and surfaces, e.g., textiles and hard surfaces. The compositions of the present invention can also be used as antimicrobial, disinfectant and/or sanitizer compositions.

Preferably the compositions are particularly suitable for use at acid or neutral pHs. According to the invention, the methods of using the compositions of enhanced bleaching employ compositions having a pH from about 1 to about 9, preferably less than about 9, less than about 8, and still more preferably less than about 7.

The compositions may be used for various applications, e.g., laundry detergent and/or bleaching, ware wash bleaching agent, hard surface cleaning and bleaching, souring and/or sanitizing, grout bleaching, and the like including antimicrobial applications customarily employing peracid compositions. In some embodiments, compositions containing compounds of the present invention can be multipurpose. That is, the compositions of the present invention can, for example, act as both antimicrobials and bleaches. The compositions of the present invention can further act as disinfection, a combination of disinfection and cleaning, virucidal treatment and/or fungicidal treatment.

According to an embodiment of the invention, a method for reducing a microbial population on a variety of surfaces, including the bleaching of a variety of surfaces are provided. The methods according to the invention can operate on an object, article, surface, or the like, by contacting the object, article or surface with a peroxycarboxylic acid bleaching composition of the invention. As one skilled in the art shall ascertain based upon the disclosure of the present invention, contacting can include any of numerous methods for applying a composition, such as spraying the composition, immersing the object in the composition, foam or gel treating the object with the composition, or a combination thereof.

A particularly suitable application of the peroxycarboxylic acid bleaching compositions includes bleaching applications, such as bleach additives. These applications may include for example, laundry detergent and/or bleaching, such as bleaching on stains, including stained fabrics. These applications further include, for example ware wash bleaching, hard surface cleaning and bleaching, souring and/or sanitizing, and grout bleaching, which may include use of the compositions to bleach stained ware (e.g. cups, plates, etc.) and stained surfaces including grout and the like.

A concentrate or use concentration of the peroxycarboxylic acid bleaching compositions can be applied to or brought into contact with an object or surface by any conventional method or apparatus for applying an antimicrobial, bleaching or cleaning composition to an object or surface. For example, the object can be wiped with, sprayed with, and/or immersed in the peracid composition, or a use composition made from the peracid composition. Contacting can be manual or by machine which may employ a liquid, gel, aerosol, gas, wax, solid, or powdered peracid compositions according to the invention, or solutions containing these compositions.

According to an embodiment of the invention, upon application of the peroxycarboxylic acid bleaching compositions the object, article or surface may be moved with mechanical action, preferably agitated, rubbed, brushed, etc. Agitation can be by physical scrubbing, through the action of the spray solution under pressure, through sonication, or by other methods. Agitation increases the efficacy of the spray solution in killing micro-organisms, perhaps due to better exposure of the solution into the crevasses or small colonies containing the micro-organisms. According to further embodiments of the invention a use solution of the peroxycarboxylic acid bleaching composition can also be used at a temperature of about 10 to 70° C., preferably about 20° C. to 60° C. to increase efficacy.

A sprayed peroxycarboxylic acid bleaching composition can be left on a treated object or surface for a sufficient amount of time to suitably reduce the staining of the surface, and then rinsed, drained and/or evaporated off the treated object or surface. The present methods require a certain minimal contact time of the peracid composition for occurrence of significant bleaching effect. The contact time can vary with concentration of the use composition, method of applying the use composition, temperature of the use composition, amount of soil on the treated object or surface, number of microorganisms on the treated object or surface, type of antimicrobial agent, or the like. Preferably the bleaching exposure time is at least about 5 seconds to about 15 minutes to about 1 hour.

Immersing an object or surface in a liquid peroxycarboxylic acid bleaching composition can be accomplished by any of a variety of methods known to those of skill in the art. For example, the object can be placed into a washer, tank or bath containing the peroxycarboxylic acid bleaching composition. Alternatively, the object can be transported or processed in a flume of the peroxycarboxylic acid bleaching composition. Alternatively, the object can be sprayed or otherwise treated with the bleaching solution. The washing solution is preferably agitated to increase the efficacy of the solution and the speed at which the solution reduces the stains on the object. Agitation can be obtained by conventional methods, including ultrasonics, aeration by bubbling air through the solution, by mechanical methods, such as strainers, paddles, brushes, pump driven liquid jets, or by combinations of these methods. The washing solution can be heated to increase the efficacy of the solution in bleaching stains. After the object has been immersed for a time sufficient for the desired bleaching effect, the object can be removed from the bath or flume and the peracid composition can be rinsed, drained, or evaporated off the object.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, patents, and patent applications cited throughout this application are hereby incorporated by reference to the same extent as if each individual publication or patent application was specifically and individually indicated as incorporated by reference. All publications and patent applications in this specification are indicative of the level of ordinary skill in the art to which this invention pertains. The invention is further illustrated by the following examples, which should not be construed as further limiting.

Methods for Industrial Processing

In some aspects, the invention includes methods of using the peroxycarboxylic acid compositions to prevent biological fouling in various industrial processes and industries, including oil and gas operations, to control microorganism growth, eliminate microbial contamination, limit or prevent biological fouling in liquid systems, process waters or on the surfaces of equipment that come in contact with such liquid systems. As referred to herein, microbial contamination can occur in various industrial liquid systems including, but not limited to, air-borne contamination, water make-up, process leaks and improperly cleaned equipment. In another aspect, the peroxycarboxylic acid compositions are used to control the growth of microorganisms in water used in various oil and gas operations. In a further aspect, the compositions are suitable for incorporating into fracturing fluids to control or eliminate microorganisms.

For the various industrial processes disclosed herein, "liquid system" refers to flood waters or an environment within at least one artificial artifact, containing a substantial amount of liquid that is capable of undergoing biological fouling, it includes but is not limited to industrial liquid systems, industrial water systems, liquid process streams, industrial liquid process streams, industrial process water systems, process water applications, process waters, utility waters, water used in manufacturing, water used in industrial services, aqueous liquid streams, liquid streams containing two or more liquid phases, and any combination thereof.

In at least one embodiment this technology would be applicable to any process or utility liquid system where microorganisms are known to grow and are an issue, and biocides are added. Examples of some industrial process water systems where the method of this invention could be applied are in process water applications (flume water, shower water, washers, thermal processing waters, brewing, fermentation, CIP (clean in place), hard surface sanitization, etc.), Ethanol/Biofuels process waters, pretreatment and utility waters (membrane systems, ion-exchange beds), water used in the process/manufacture of paper, ceiling tiles, fiber board, microelectronics, E-coat or electro deposition applications, process cleaning, oil exploration and energy services (completion and work over fluids, drilling additive fluids, fracturing fluids, flood waters, etc.; oil fields—oil and gas wells/flow line, water systems, gas systems, etc.), and in particular water systems where the installed process equipment exhibits lowered compatibility to halogenated biocides.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, patents, and patent applications cited throughout this application are hereby incorporated by reference to the same extent as if each individual publication or patent application was specifically and individually indicated as incorporated by reference. All publications and patent applications in this specification are indicative of the level of ordinary skill in the art to which this invention pertains. The invention is further illustrated by the following examples, which should not be construed as further limiting.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

The materials used in the following Examples are provided herein:

Oxonia Active®: a peroxyacetic acid antimicrobial agent (5.8% peroxyacetic acid, 27.5% hydrogen peroxide), available from Ecolab Inc.

Bleach Activator: polyethyleneimine derivatized with ethylenediamine, molecular weight 800, available from Aldrich Chemical.

Example 1

The bleaching efficacy of compositions according to the invention were compared to untreated peracid compositions and bleaching activators alone (without a peracid) to determine whether the bleach activators according to the invention provide improvements in bleaching performance of peracid compositions. The various compositions were added to a 2% red dye solution in a beaker. The solution was then monitored using a spectrometer set at 350 nm for disappearance of the dye as indicated by an increase in % transmittance through the dye solution.

Figure 1:
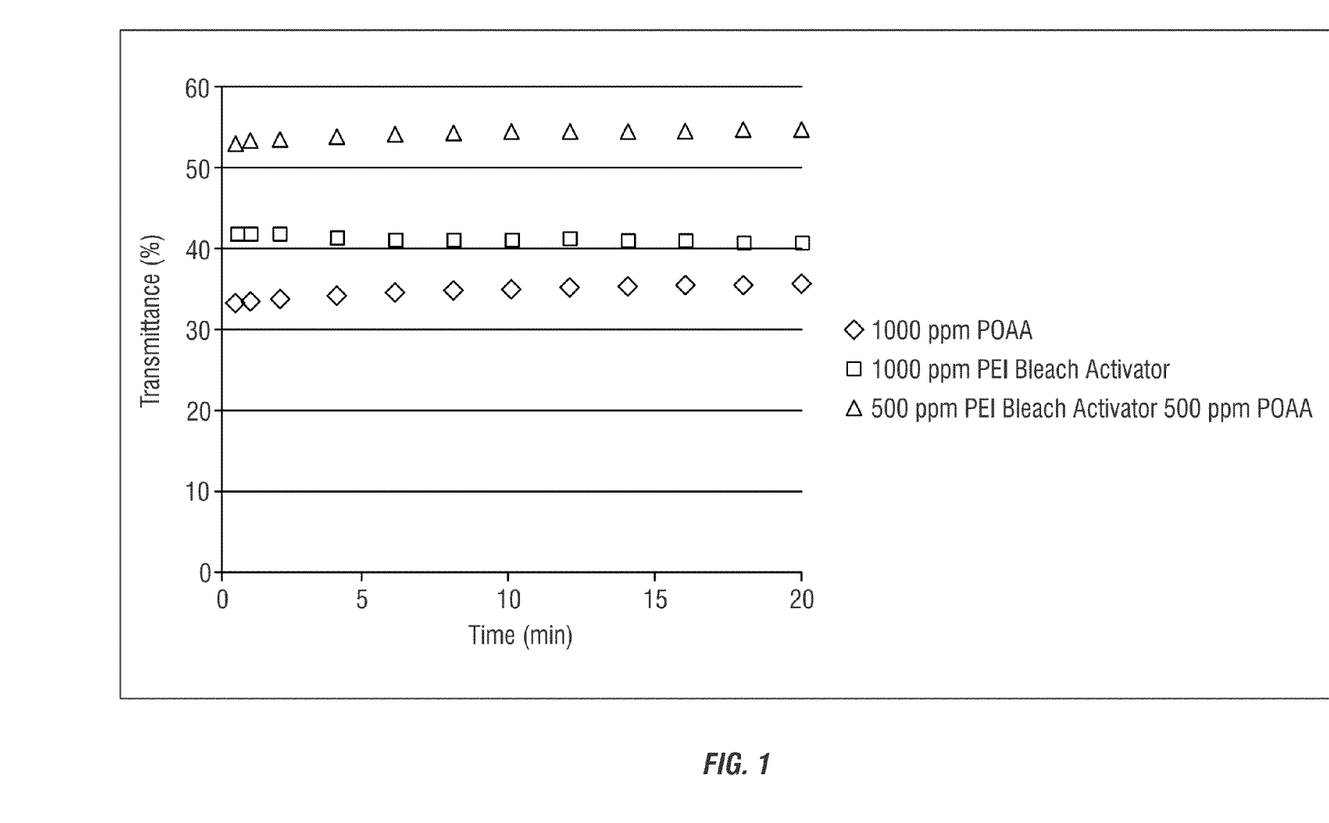
FIG. 1 shows a comparison according to the invention between an untreated peracid composition, a polyethyleneimine bleach activator without a peracid composition and a bleaching composition according to the invention in bleaching performance.

FIG. 1 shows the transmittance of samples with constant total chemistry. As shown in FIG. 1, as a baseline comparison, an untreated peracid (POAA, peroxyacetic acid 1000 ppm), a polyethyleneimine (PEI) solution without peracid, and a combination of reduced concentrations of peracid and bleach activator (POAA 500 ppm, polyethyleneimine 500 ppm) were compared. The combination of peracid and polyethyleneimine provided the greatest amount of bleaching activity, despite the 50% reduction in active percentage.

Example 2

As a result of the enhanced bleaching performance achieved in Example 1 as a result of combining the bleach activator polyethyleneimine with a peracid composition according to the invention, additional experimentation was conducted to determine the effect of concentration on bleaching efficacy.

Figure 2:
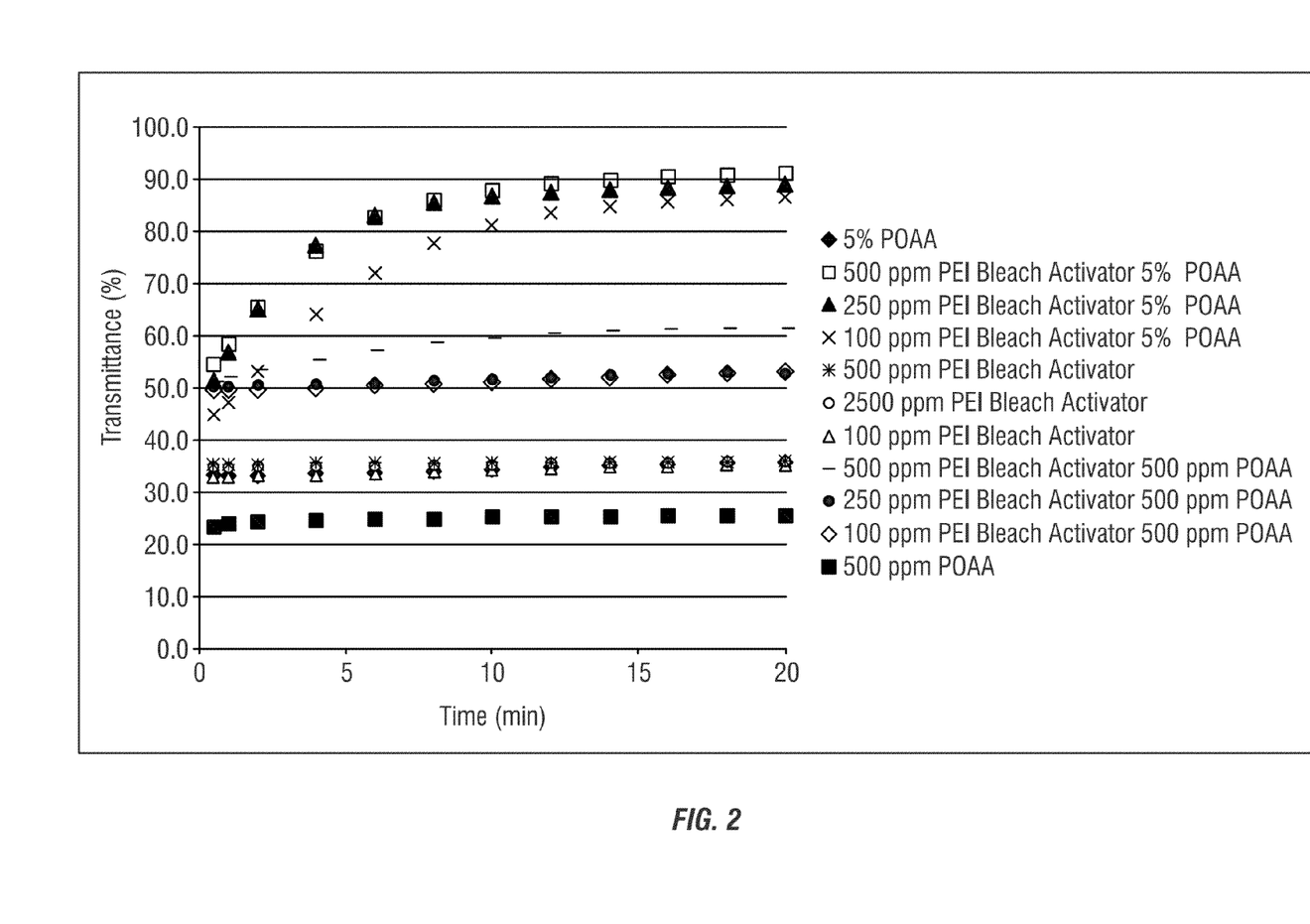
FIG. 2 shows the efficacy of various concentrations of polyethyleneimine bleach activators according to the invention in activating a peracetic acid composition.
Figure 3:
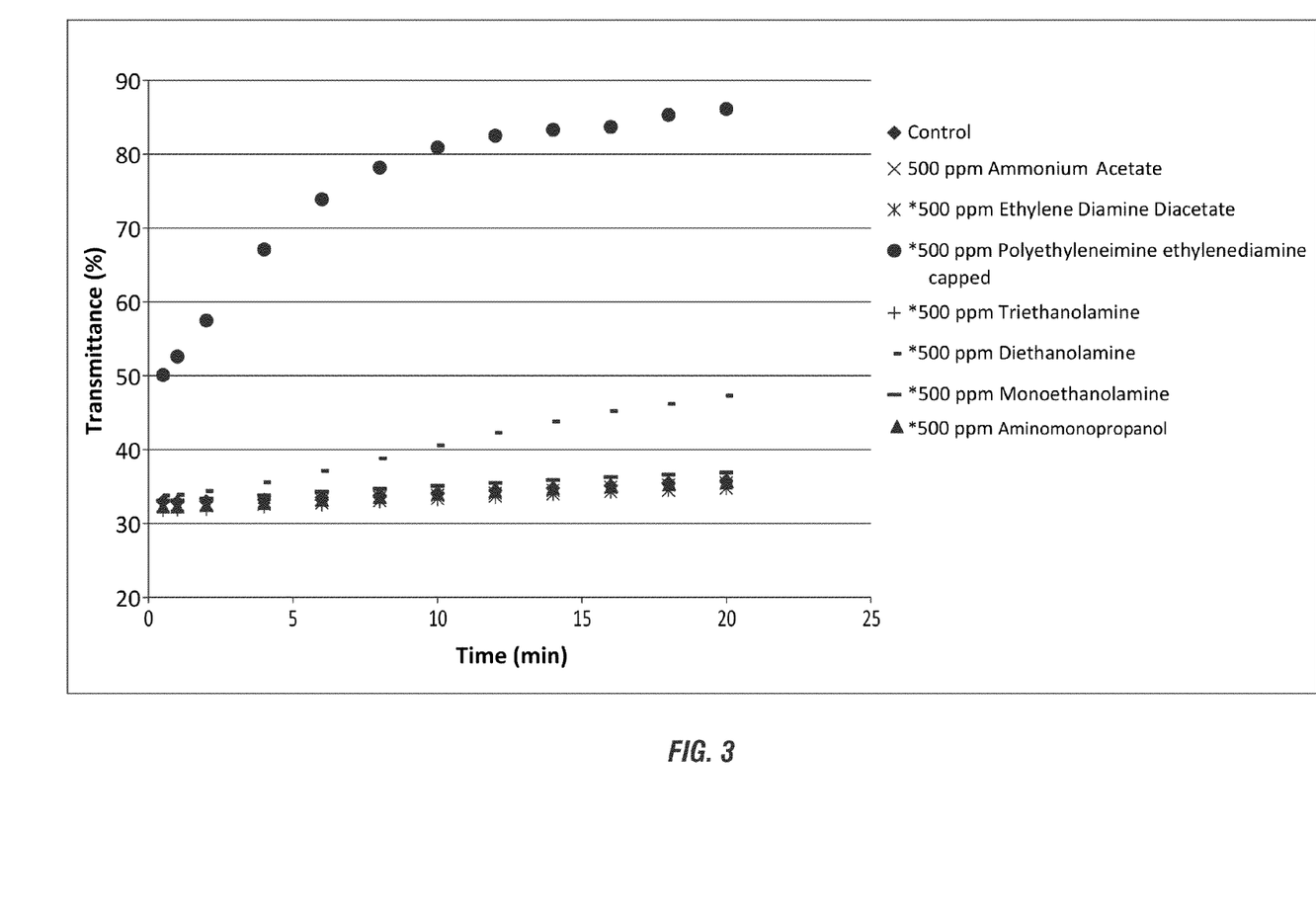
FIG. 3 shows the efficacy of a polyethyleneimine bleach activator according to the invention in activating a peracetic acid composition to provide enhanced bleaching efficacy.

Various compositions of untreated peracetic acid, polyethyleneimine (PEI) without peracids and combinations of the peracid with the polyethyleneimine bleach activator were compared using the methods of Example 1. The polyethyleneimine bleach activator employed was an ethylenediamine-modified polyethyleneimine. FIG. 2 shows the various concentrations of each composition evaluated and comparisons of the varying ratios between the polyethyleneimine bleach activator and the peracid.

The transmittance of the polyethyleneimine and Oxonia samples described in this Example are shown in FIG. 2. Beneficially, the polyethyleneimine bleach activator provides a clear activation of the peracetic acid as a bleaching agent. Superior bleaching performance was achieved with each combination of a bleach activators and peracid in comparison to the peracid alone.

Example 3

Peracid compositions with various potential bleach activators (Table 3) were compared as in the above dye test for bleaching performance. The peracid used in this experiment was Oxonia Active®, Ecolab Inc. As needed to maintain a constant pH, the compositions were pre-neutralized with acetic acid (*).

TABLE 3

| Additive | Mass of Oxonia Added | Mass of Additive Added | Mass of Glacial Acetic Acid Added | Oxidizing/ Bleaching Improvement |
|---|---|---|---|---|
| Ammonium Acetate | 50.1 | 3.06 | 0 | No |
| Ethylene Diamine Diacetate* | 50.05 | 1.43 | 3.01 | No |
| Polyethyleneimine Ethylenediamine End-Capped* | 50.02 | 2.05 | 4.02 | Yes |
| Triethanolamine* | 50 | 5.94 | 10.09 | No |
| Diethanolamine* | 50.03 | 4.19 | 10.37 | No |
| Ethanolamine* | 50.13 | 2.43 | 5.03 | No |
| Aminomonopropanol* | 49.99 | 2.96 | 6.02 | No |
| Ammonium Sulfate | 49.99 | 5.27 | 0 | No |
| Control | 61.46 | None | 0 | N/A |

As shown in Table 3, the polyethyleneimine bleach activator was the only compound capable of providing enhanced bleaching activity according to the compositions and methods of the invention. The results are shown graphically in FIG. 4.

The inventions being thus described, it will be obvious that the same may be varied in many ways. Such variations are not to be regarded as a departure from the spirit and scope of the inventions and all such modifications are intended to be included within the scope of the following claims.

What is claimed is:

1. An enhanced bleaching peroxycarboxylic acid composition comprising:
   at least one peroxycarboxylic acid; and
   a non-metal bleach activator, wherein the bleach activator is a polymeric nitrogen-containing compound that is effective for enhanced bleaching in comparison to the peroxycarboxylic acid alone and is present in a use solution in amounts from about 1 ppm to about 5000 ppm, and wherein the composition has a pH less than about 9.

2. The composition of claim 1, wherein the bleach activator is a polymeric amine having a molecular weight from about 100 to about 2,000,000.

3. The composition of claim 1, wherein the bleach activator is a substituted or non-substituted polyethyleneimine.

4. The composition of claim 1, wherein the at least one peroxycarboxylic acid is an alkyl peroxycarboxylic acid.

5. The composition of claim 1, wherein at least one peroxycarboxylic acid is a $C_1$-$C_{20}$ alkyl peroxycarboxylic acid.

6. The composition of claim 1, wherein a ready to use composition comprises from about 0.01 wt % to 5 wt-% peroxycarboxylic acid and from about 1 ppm to about 1000 ppm bleach activator.

7. The composition of claim 1, further comprising an oxidizing agent comprising hydrogen peroxide, water and/or a surfactant.

8. The composition of claim 1, having a pH less than about 8.

9. An enhanced bleaching peroxycarboxylic acid composition comprising:
   about 0.01 wt-% to 50 wt-% of at least one peroxycarboxylic acid; and
   about 0.0001 wt-% to 20 wt-% of a non-metal, polyethyleneimine bleach activator, wherein the bleach activator is effective for providing enhanced bleaching in comparison to the peroxycarboxylic acid alone and is present in a use solution in amounts from about 1 ppm to about 5000 ppm, and wherein the composition has a pH less than about 9.

10. The composition of claim 9, wherein the bleach activator is a substituted polyethyleneimine.

11. The composition of claim 10, wherein the substituted polyethyleneimines bleach activator has a substituent selected from the group consisting of ethoxylates, propoxylates and combinations thereof.

12. The composition of claim 9, wherein a ready to use composition comprises from about 0.01 wt % to 5 wt-% peroxycarboxylic acid and from 10 ppm to about 500 ppm bleach activator.

13. The composition of claim 9, wherein a concentrate composition comprises from about 1 wt-% to 50 wt-% peroxycarboxylic acid and from about 1 ppm to about 50000 ppm bleach activator.

14. The composition of claim 9, further comprising water, a surfactant, at least one carboxylic acid or an oxidizing agent comprising hydrogen peroxide.

15. A method of enhancing bleaching performance of peracid composition, comprising:
   providing a bleach activator to a peroxycarboxylic acid composition to form a peroxycarboxylic acid bleaching composition comprising: about 0.01 wt-% to 50 wt-% of at least one peroxycarboxylic acid; and about 0.0001 wt-% to 20 wt-% of a non-metal, polyethyleneimine bleach activator, wherein the bleach activator is effective for providing enhanced bleaching in comparison to the peroxycarboxylic acid alone and is present in a use solution in amounts from about 1 ppm to about 5000 ppm, and wherein the composition has a pH less than about 9; and
   contacting an object with peroxycarboxylic acid bleaching composition.

16. The method of claim 15, wherein the object is a stained surface requiring bleaching, wherein the stained surface is selected from the group consisting of ware, textiles, grout, or a combination thereof.

17. The method of claim 15, further comprising generating a cationic polymer from the bleach activator in the presence of a neutralizing acid, wherein the neutralizing acid includes the peroxycarboxylic acid, and wherein the cationic polymer is the acid salt of the bleach activator.

18. The method of claim 17, wherein the cationic polymer provides improved bleaching performance of the peroxycarboxylic acid bleaching composition and enhanced attraction to negatively charged substrates.

19. The method of claim 15, wherein the bleach activator is provided to the peroxycarboxylic acid composition through a co-fed stream to form a use solution.

20. The method of claim 15, wherein the bleach activator is provided to the peroxycarboxylic acid composition in a pre-formulated concentrate or ready-to-use composition.

* * * * *